US00PP23979P2

(12) United States Plant Patent
van Noort

(10) Patent No.: US PP23,979 P2
(45) Date of Patent: Oct. 8, 2013

(54) ***ECHINACEA* PLANT NAMED 'ECCENTRIC'**

(50) Latin Name: *Echinacea purpurea*
Varietal Denomination: Eccentric

(76) Inventor: Marco van Noort, Warmond (NL)

( * ) Notice: Subject to any disclaimer, the term of this patent is extended or adjusted under 35 U.S.C. 154(b) by 78 days.

(21) Appl. No.: 13/385,810

(22) Filed: Mar. 7, 2012

(51) Int. Cl.
*A01H 5/00* (2006.01)

(52) U.S. Cl.
USPC ..... Plt./428

(58) Field of Classification Search
USPC ..... Plt./428
See application file for complete search history.

*Primary Examiner* — Annette Para
(74) *Attorney, Agent, or Firm* — Penny J. Aguirre

(57) ABSTRACT

A new cultivar of hybrid *Echinacea*, 'Eccentric', characterized by its anemone-type inflorescences (semi-double) with ray florets and disk florets that are initially red-purple in color and mature to orange-red; disk florets exhibit an enlarged petal and its numerous flowering stems that are strong and held upright, its floriferous habit, and it compact and short plant habit.

2 Drawing Sheets

Botanical classification: *Echinacea purpurea.*
Variety denomination: 'Eccentric'.

BACKGROUND OF THE INVENTION

The present Invention relates to a new and distinct cultivar of *Echinacea purpurea* and will be referred to hereafter by its cultivar name, 'Eccentric'. 'Eccentric' represents a new coneflower, an herbaceous perennial grown for landscape use.

The new cultivar arose from an ongoing breeding program conducted by the Inventor in a designated field at his nursery in Warmond, The Netherlands. The goal of his breeding program is to create new cultivars of *Echinacea* that exhibit flowers with attractive form and coloration. The Inventor made a cross in 2009 between unnamed plants of *Echinacea purpurea* from his breeding line. 'Eccentric' was selected by the Inventor as a single unique plant amongst the resulting seedlings from the above cross in June of 2010.

Asexual reproduction of the new cultivar was first accomplished by division in Warmond, The Netherlands in summer of 2010 by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Eccentric' as a unique cultivar of *Echinacea.*

1. 'Eccentric' exhibits strong, upright stems.
2. 'Eccentric' exhibits numerous flowering stems.
3. 'Eccentric' exhibits anemone-type inflorescences (semi-double) with ray florets and disk florets that are initially red-purple in color and mature to orange-red; disk florets exhibit enlarged petals.

The female parent of 'Eccentric' differs from 'Eccentric' in having single inflorescences. The male parent of 'Eccentric' differs from 'Eccentric' in having inflorescences that are less intense in color. 'Eccentric' can be most closely compared to the cultivars 'Razzmatazz' (U.S. Plant Pat. No. 13,894) and 'Irresistible' (U.S. Plant Pat. No. 20,756). Both are similar to 'Eccentric' in having semi-double inflorescences. 'Razzmatazz' differs from 'Eccentric' in having inflorescences that are rose pink to purple-pink in color. 'Irresistible' differs from 'Eccentric' in having inflorescences that are orange to red-orange in color.

BRIEF DESCRIPTION OF THE DRAWING

The plants and plant parts in the accompanying photographs depict a six-month-old plant of 'Eccentric' as field grown (containerized for the photographs) in Warmond, The Netherlands.

The photograph in FIG. 1 provides a side view of 'Eccentric' in bloom.

Figure 1:
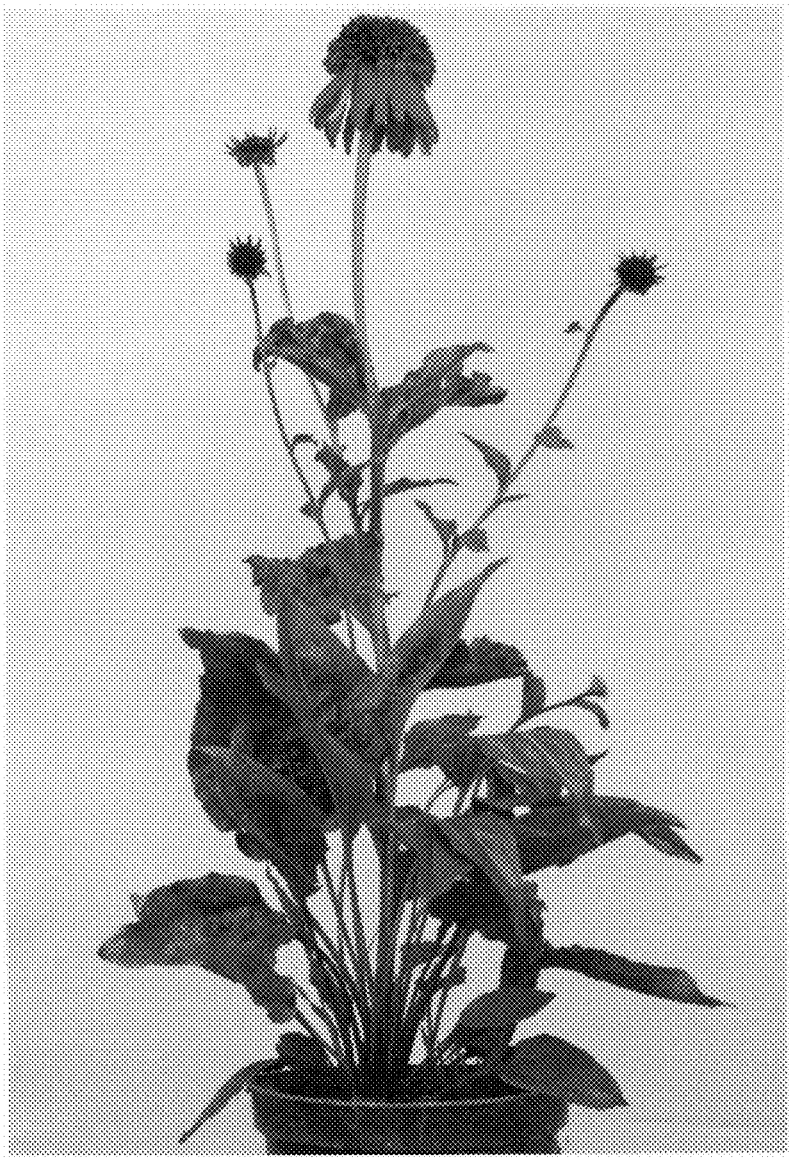
Figure 2:
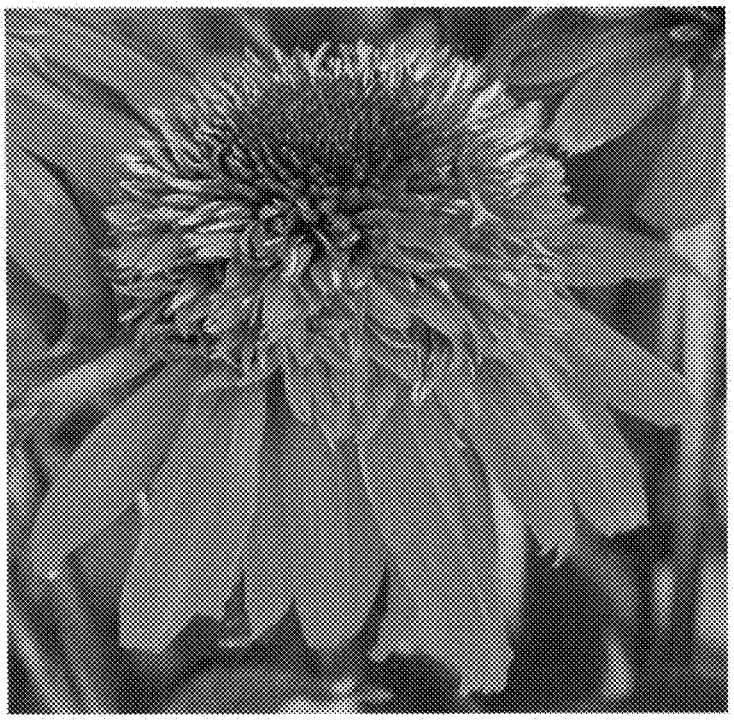

The photograph in FIG. 2 shows a close-up of an inflorescence of 'Eccentric'.

Figure 3:
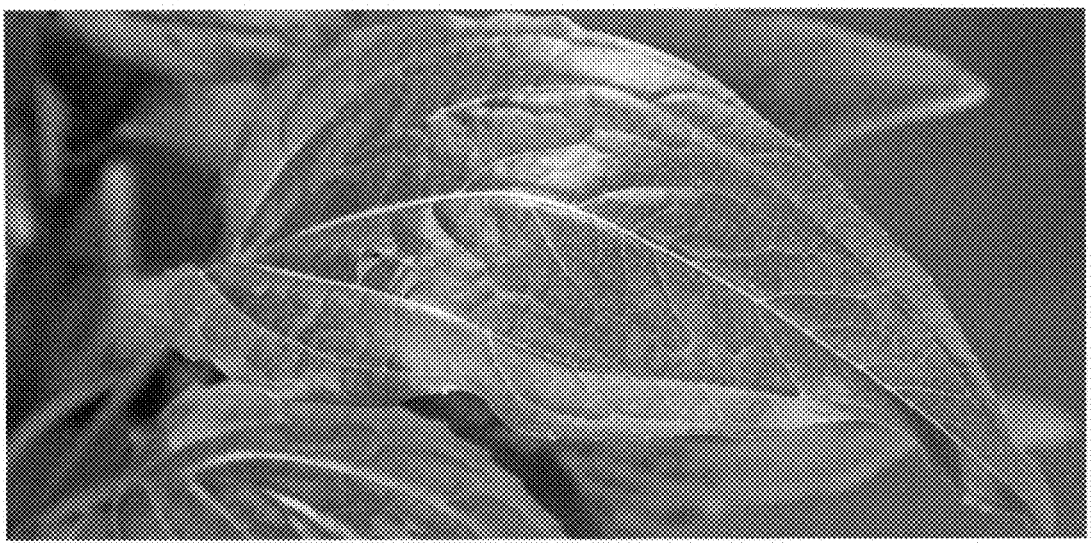

The photograph in FIG. 3 provides a close-up view of a leaf of 'Eccentric'.

The colors in the photograph may differ slightly from the color values cited in the detailed botanical description, which accurately describe the colors of the new *Echinacea.*

BOTANICAL DESCRIPTION OF THE PLANT

The following is a detailed description of a six-month-old plant of the new cultivar as grown outdoors in a test garden in Warmond, The Netherlands. The plants were grown under average day temperatures of 14° to 28° C. and average night temperatures of 6° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from early July to late September in The Netherlands.

*Plant habit.*—Herbaceous perennial, clump forming, upright.

*Height and spread.*—Reaches about 65 cm in height 40 cm in spread.

*Hardiness.*—U.S.D.A. Zones 3 to 4.

*Diseases resistance.*—Not more susceptible to pests/diseases than other *Echinacea* varieties.

*Root description.*—Fibrous.

Growth and propagation:

*Propagation.*—Division, vegetative stem cuttings, and tissue culture.

*Growth rate* .—Moderately vigorous.

Stem description:

*Shape.*—Rounded, solid.

*Stem color.*—144A, tinged with 182B.

*Stem size.*—An average of 1.1 cm in diameter and 39.2 cm in length excluding inflorescence.

*Stem strength.*—Strong.

*Stem aspect.*—Held upright, stems grow in an average angle of 5° from the base.

*Stem surface.*—Moderately rough to touch and sparsely covered with short strigose hairs about 0.5 mm in length and 157D in color.

*Stem number.*—Average of 4 main stems.

*Internode length.*—Average of 5.9 cm in length.

*Branching.*—Main flowering stem with an average of 4 lateral branches.

Foliage description:

*Leaf shape.*—Ovate.

*Leaf division.*—Simple.

*Leaf base.*—Attenuate.

*Leaf apex.*—Acute.

*Leaf venation.*—Pinnate, color: upper surface; 148A to 148B, lower surface; 144B.

*Leaf margins.*—Entire and undulate.

*Leaf attachment.*—Petiolate.

*Leaf arrangement.*—Alternate.

*Leaf size.*—Average of 14.2 cm in length and 7.1 cm in width.

*Leaf color.*—Young upper surface; 143A, young lower surface; 146B, mature upper surface; N137B, mature lower surface; 137B.

*Leaf surface.*—Upper and lower surface is moderately glossy, and sparsely covered with short strigose hairs about 0.3 mm in length and 157D in color.

*Petioles.*—Upper stem leaves nearly sessile, average of 12.4 cm in length and 4 mm in width, upper surface; 144B to 144C in color, lower surface; 144B to 144C in color, upper and lower surfaces are smooth.

Flower description:

*Type.*—Capitulum, heterogamous with ray florets around the head margin and disk florets with expanded ray floret-like petal, anemone-type (referred to as semi-double).

*Capitulum number.*—An average of 1 per stem.

*Lastingness of inflorescence.*—About 2 to 3 weeks.

*Capitulum size.*—Matures to about 7.8 cm in height and 9.4 cm in diameter, disk is about 7.6 cm in diameter.

*Fragrance.*—None.

*Involucral bracts or phyllary.*—About 45 arranged in 3 overlapping rows, average of 1.0 cm in length and 3 mm in width, cuneate base, acute apex, narrow ovate in shape, upper surface is 143A in color, lower surface ranges from 143A to 143B in color, margins entire and sparsely covered with short hairs about 0.2 mm in length and close to 157D in color, smooth on upper and lower surface.

*Buds.*—Flattened globular in shape, immature ray florets near vertical (upright), an average of 2 cm in length and 3 cm in diameter, color; 144A, spines 166B, immature ray florets 184C tipped with N144A.

*Peduncle.*—Strong, terminal is an average of 33 cm in length and 7 mm in diameter with axillary peduncles ($4^{th}$) an average of 36 cm in length and 7 mm in diameter, terminals held upright with axillary peduncle held at an average angle of 25° to vertical, color; 144A, tinged with 182B, surface is sparsely covered with short strigose hairs about 0.5 mm in length and 157D in color.

*Ray florets* (*sterile*).—Rotate, average of 22 per inflorescence, oblanceolate to narrow oblanceolate in shape, convexed, upper surface smooth, dull and velvety with moderately ribbed lengthways in texture, lower surface smooth and slightly glossy with moderately ribbed lengthways in texture, about 7 cm in length and 2 cm in width, praemorse apex, cuneate base, entire margin, strongly drooping in an average angle of about 40° downward from horizontal, color of upper surface when opening; 46A, color of lower surface when opening; ranges from 54C to 54D to 58A with tips tinged 145A, color of upper surface when fully open; 45A to 45B, color of lower surface when fully open; ranges from 54A to 54D to 58A with tips tinged with 145A, non fading.

*Disk flowers* (*bisexual*).—Numerous, about 300, tubular in shape with lower 60% fused into tube, arranged spirally on disc, apex is narrowly acute, fused base, entire margin, average of 2.8 cm in length and 1.3 cm in width, upper surface is smooth, dull and velvety, lower surface is smooth, dull and slightly glossy, color when opening upper surface; 41A to 41B, color of lower surface when opening; 45C to 46C, color of upper surface when fully open; 41A to 41B, color of lower surface when fully open; 45C to 46C.

*Disk spines.*—Average of 300, acicular in shape, acute apex, attenuate base, smooth and glossy surface, color is 46A at apex, 21A in mid region and 144A to 144B at base.

*Receptacle.*—Triangular in shape, an average of 14 mm in height and 15 mm in diameter, and 155B in color.

Reproductive organs (present on disk florets only):

*Gynoecium.*—Pistil; 1, 8.5 mm in length, style; about 7 mm in length and 165C in color, stigma; unequal, decurrent and 187A in color, ovary; 145D in color.

*Androcoecium.*—Stamens; 4, filaments; 3 mm in length and N200B in color, anthers; linear in shape, about 3 mm in length and 203C in color, pollen; none observed.

*Fruit/seed.*—No seed production has been observed.

It is claimed:

1. A new and distinct cultivar of *Echinacea* plant named 'Eccentric' substantially as herein illustrated and described.

* * * * *